United States Patent
Kuratani et al.

(10) Patent No.: US 9,879,291 B2
(45) Date of Patent: Jan. 30, 2018

(54) CONTINUOUS PRODUCTION OF BIODIESEL FUEL BY ENZYMATIC METHOD

(71) Applicants: Kansai Chemical Engineering Co., Ltd., Amagasaki-shi, Hyogo (JP); Bio-energy Corporation, Amagasaki-shi, Hyogo (JP)

(72) Inventors: Nobuyuki Kuratani, Amagasaki (JP); Shinji Hama, Amagasaki (JP); Hideo Noda, Amagasaki (JP); Hideki Fukuda, Kobe (JP)

(73) Assignees: Kansai Chemical Engineering Co., Ltd., Hyogo (JP); Bio-Energy Corporation, Hyogo (JP)

( * ) Notice: Subject to any disclaimer, the term of this patent is extended or adjusted under 35 U.S.C. 154(b) by 193 days.

(21) Appl. No.: 14/741,755

(22) Filed: Jun. 17, 2015

(65) Prior Publication Data

US 2015/0284748 A1 Oct. 8, 2015

Related U.S. Application Data

(62) Division of application No. 12/745,962, filed as application No. PCT/JP2008/072111 on Nov. 28, 2008, now abandoned.

(30) Foreign Application Priority Data

Dec. 14, 2007 (JP) ................................. 2007-323381

(51) Int. Cl.
- C12P 7/62 (2006.01)
- C12P 7/64 (2006.01)
- C11C 3/00 (2006.01)

(52) U.S. Cl.
CPC .............. *C12P 7/649* (2013.01); *C11C 3/003* (2013.01); *C12P 7/62* (2013.01);
(Continued)

(58) Field of Classification Search
CPC .................................... C12P 7/62; C12P 7/649
See application file for complete search history.

(56) References Cited

U.S. PATENT DOCUMENTS

| 6,982,155 B1 | 1/2006 | Fukuda et al. |
| 2006/0063242 A1 | 3/2006 | Chou |

(Continued)

FOREIGN PATENT DOCUMENTS

| CN | 200967808 Y | 10/2007 |
| EP | 1851294 | 8/2006 |

(Continued)

OTHER PUBLICATIONS

Extended European Search Report dated Mar. 29, 2011 received in European Application No. 2241631.

(Continued)

*Primary Examiner* — William H. Beisner
(74) *Attorney, Agent, or Firm* — Ajay A. Jagtiani; Miles & Stockbridge P.C.

(57) ABSTRACT

A method for continuously producing a fatty acid ester of the present invention comprises (a) mixing and agitating an oil and fat starting material and a lower alcohol, and supplying a mixture to one of the catalyst reaction tubes filled with a lipase; (b) producing a fatty acid ester and glycerin in the catalyst reaction tube; (c) introducing an outflowing liquid from the catalyst reaction tube into a glycerin separation tank, thereby collecting the glycerin; (d) adding a lower alcohol to a separated liquid obtained by separating the glycerin from the outflowing liquid, mixing and agitating an obtained material, and supplying a mixture to a following catalyst reaction tube; (e) repeating the steps (b) to (d) until supply to a last catalyst reaction tube is performed; and (f) collecting a fatty acid ester from the separated liquid obtained from the last catalyst reaction tube. According to the method of the present invention, the concentration of a lower alcohol can be strictly controlled and by-product glycerin can be automatically removed.

7 Claims, 6 Drawing Sheets

(52) U.S. Cl.
CPC ....... *C10G 2300/1011* (2013.01); *Y02E 50/13* (2013.01); *Y02P 30/20* (2015.11)

(56) References Cited

U.S. PATENT DOCUMENTS

| | | | |
|---|---|---|---|
| 2007/0232818 A1 | 10/2007 | Crawford et al. | |
| 2009/0069586 A1 | 3/2009 | Oku et al. | |

FOREIGN PATENT DOCUMENTS

| | | | |
|---|---|---|---|
| JP | 63059896 | A | 3/1988 |
| JP | 2005-350632 | A | 12/2005 |
| WO | 00/12743 | A1 | 3/2000 |
| WO | 01/038553 | A1 | 5/2001 |
| WO | 2006088254 | A2 | 8/2006 |
| WO | 2007043552 | A1 | 4/2007 |
| WO | 2007/130346 | A1 | 11/2007 |

OTHER PUBLICATIONS

Notification of Transmittal of Translation of the International Preliminary Report on Patentability received in PCT/JP2008/072111, dated Jul. 29, 2010.

K. Belafi-Bako, et al., "Enzymatic Biodiesel Production from Sunflower Oil by Candida Antarctica Lipase in a Solvent-free System", Biocatalysis and Biotransformation, vol. 20, No. 6, pp. 437-439 (2002).

Hideki Fukuda, et al., "Biodiesel Fuel Production by Transesterification of Oils", Journal of Bioscience and Bioengineering, vol. 92, No. 5, pp. 405-416 (2001).

Enoch Y. Park, et al., "Lipase-catalyzed biodiesel production from waste activated bleaching earth as raw material in a pilot plant", Bioresource Technology, vol. 99, pp. 3130-3135 (2008).

Yuji Shimada, et al., "Conversion of Vegetable Oil to Biodiesel Using Immobilized Candida Antarctica Lipase", JAOCS, vol. 76, No. 7, pp. 789-793 (1999).

Yomi Watanabe, et al., "Continuous Production of Biodiesel Fuel from Vegetable Oil Using Immobilized Candida Antarctica Lipase", JAOCS, vol. 77, No. 4, pp. 355-360 (2000).

Yuanyuan Xu, et al., "Conversion of Soybean Oil to Biodiesel Fuel Using Lipozyme TL IM in a Solvent-free Medium", Biocatalysis and Biotransformation, vol. 22, No. 1, pp. 45-48 (2004).

Shimada, Y., et al., Enzymatic alcoholysis for biodiesel fuel production and application of the reaction to oil processing, 2002, Journal of Molecular Catalysis B: Enzymatic, pp. 133-142.

Hama, et al."Biodiesel-fuel production in a packed-bed reactor using lipase-producing Rhizopus oryzae cells immobilized within biomass support particles", Biochemical Engineering Journal, vol. 34, pp. 273-278 (2007).

Nie, et al., "Lipase catalyzed methanolysis to produce biodiesel: Optimization of the biodiesel production", Journal of Molecular Catalysis B: Enzymatic, vol. 43, pp. 142-147 (2006).

PCT International Search Report received in PCT/JP2008/072111 dated Jan. 20, 2009.

CONTINUOUS PRODUCTION OF BIODIESEL FUEL BY ENZYMATIC METHOD

TECHNICAL FIELD

The present invention relates to a method for continuously producing a fatty acid ester useful as a biodiesel fuel using an enzymatic method, and an apparatus for the same.

BACKGROUND ART

In general, fossil fuels typified by petroleum and light oil are used as fuels for automobiles. Those fossil fuels, especially, light oil used for diesel automobiles, contain a large amount of nitrogen compound and sulfur compound, so that a large amount of gas such as $CO_2$, NOx, SOx is exhausted from automobiles such as diesel automobiles. Since these exhaust gases cause global warming and environmental pollution, reduction of the exhaust amount is an issue to be solved urgently.

As an alternative fuel to fossil fuels such as light oil, there are high expectations in so-called biodiesel fuel, which uses oils and fate produced by naturally-occurring plants, animals, fishes, or microorganisms. Among these oils and fats, those used for food producing are often dumped into the environment and cause environmental problems. Therefore, expectations in biodiesel fuel made from a waste oil are particularly high in view of prevention of air pollution and effective utilization of a waste oil.

Fatty acid esters obtained by transesterification between an oil and fat and a lower alcohol are preferably used as biodiesel fuels. A variety of researches have been conducted on an enzyme-catalytic method using a lipase, as one method for producing a fatty acid ester (International Publications WO 01/088668 and WO 00/12748). This production method has many advantages, for example, in that aftertreatment of by-product glycerin is easy, in that mild reaction conditions can be applied, and in that a free fatty acid in a starting material can be esterified (H. Fukuda at al., Journal of Bioscience and Bioengineering, 2001, Vol. 92, pp. 405-416).

Regarding production of a fatty acid ester using a lipase, researches have been intensively conducted on a batch-type transesterification in which an enzyme, an oil and fat, and a lower alcohol are agitated and mixed in a screw cap bottle or a reaction tank (Y. Shimada at al., Journal of the American Oil Chemists' Society, 1999, Vol. 76, pp. 789-793, and E. Y. Park et al., Bioresource Technology, 2008, Vol. 99, No. 8, pp. 8180-8185). In this method, it is necessary to be careful of physical damage to the enzyme due to agitation of the reaction mixture. Furthermore, in order to collect a product after the reaction, it is necessary to perform a procedure that separates a product, an enzyme, and a by-product into layers after stopping agitation and allowing the reaction mixture to stand.

On the other hand, there is a report on production of a fatty acid ester using a packed-bed reactor of a tube filled with a lipase through which an oil and fat and a lower alcohol pass (Y. Watanabe et al., Journal of the American Oil Chemists' Society, 2000, Vol. 77, pp. 855-860, and K. Nie et al., Journal of Molecular Catalysis B: Enzymatic, 2006, Vol. 43, pp. 142-147). In this case, the enzyme is fixed in the tube, and, thus, the degree of physical damage to the enzyme is low, and the operation can be performed for a long period of time. Moreover, since the reactor can be filled with a large amount of enzyme, the method has a feature that there is a significant increase in the amount of target substance produced per reactor unit volume and per reaction time. In researches using a packed-bed reactor, typical examples of which are shown by Y. Watanabe et al. (Journal of the American Oil Chemists' Society, 2000, Vol. 77, pp. 855-860) and K. Nie et al. (Journal of Molecular Catalysis B: Enzymatic, 2006, Vol. 48, pp. 142-147), a method is applied in which an oil and fat and a lower alcohol are supplied from an upper portion of a reaction tube, a reaction mixture that has flown out of a lower portion thereof is temporarily allowed to stand so as to be separated into layers, and then a fatty acid ester in an upper layer (also containing unreacted oil and fat) is collected.

In general, a lower alcohol inhibits the activity of a lipase, and thus it is necessary to strictly control the ratio of lower alcohol contained in the reaction mixture. Furthermore, since the solubility of a lower alcohol in an oil and fat is extremely low, it is necessary to keep a uniformly dispersed state such that a droplet of the alcohol is not formed in the oil and fat (Y. Shimada at al., Journal of Molecular Catalysis B: Enzymatic, 2002, Vol. 17, pp. 188-142). There is also a method for reducing the alcohol inhibition by dissolving the reaction mixture in a hydrophobic organic solvent, such as hexane. However, according to the method the collection of the product is difficult, and the production process is complicated.

Glycerin forms as a by-product during a procedure for producing a fatty acid ester. A certain amount of the glycerin accumulated forms a layer around the enzyme. Since this layer of glycerin is hydrophilic, it greatly affects the contact efficiency between unreacted oil and fat and the enzyme. Moreover, part of a lower alcohol remaining in the reaction procedure is dispersed in the glycerin layer, and locally increases the concentration of alcohol near the enzyme, so that a lowered enzymatic activity is caused (Y. Watanabe et al., Journal of the American Oil Chemists' Society, 2000, Vol. 77, pp. 855-860). Conventionally, there is a report on an attempt to remove glycerin by dialysis or by using an organic solvent such as isopropanol (K. B. Bako et al., Biocatalysis and Biotransformation, 2002, Vol. 20, pp. 487-489, and Y. Xu et al., Biocatalysis and Biotranformation, 2004, Vol. 22, pp. 45-48). However, there is a demand for a method for more easily removing glycerin, in view of industrialization of the process.

One aspect is that a method for continuously collecting a product for a long period of time while supplying starting materials is desirable, and use of a packed-bed reactor is advantageous for industrial production of a biodiesel fuel using a lipase. However, another aspect is that it is necessary to be careful of the possibility that a desirable yield of fatty acid ester may not be obtained depending on the supply of an oil and fat and a lower alcohol to a reaction tube and the removal efficiency of by-product glycerin as described above. Therefore, it is necessary to establish a method for continuously producing a biodiesel fuel simultaneously considering these two aspects.

DISCLOSURE OF INVENTION

The object of the present invention is to provide a process capable of strictly controlling the concentration of a lower alcohol while automatically removing by-product glycerin in the production of a fatty acid ester from oils and fats using a lipase.

The present invention provides a method for continuously producing a fatty acid ester in a reaction apparatus having a plurality of stages of catalyst reaction tubes filled with a lipase, comprising:

(a) mixing and agitating an oil and fat starting material and a lower alcohol, and supplying a mixture to one of the catalyst reaction tubes;

(b) producing a fatty acid eater and glycerin in the catalyst reaction tube to which the oil and fat starting material and the lower alcohol are supplied;

(c) introducing an outflowing liquid from the catalyst reaction tube into a glycerin separation tank, thereby collecting the glycerin;

(d) adding a lower alcohol to a separated liquid obtained by separating the glycerin from the outflowing liquid, mixing and agitating an obtained material, and supplying a mixture to a following catalyst reaction tube;

(e) repeating the steps (b) to (d) until supply to a last catalyst reaction tube is performed;

(f) introducing an outflowing liquid from the last catalyst reaction tube into a glycerin separation tank placed downstream of the last catalyst reaction tube, thereby collecting glycerin, and obtaining a separated liquid obtained by separating the glycerin from the outflowing liquid; and (g) collecting a fatty acid ester from the separated liquid obtained in the step (f).

In an embodiment, a liquid flow rate in the reaction apparatus is at least 2.16 cm/min.

In one embodiment, an amount of the lower alcohol supplied to each of the catalyst reaction tubes is 0.5 to 1.0 mol equivalent with respect to the oil and fat starting material.

In a further embodiment, the number of stages of the catalyst reaction tubes is 2 to 10.

In an embodiment, the oil and fat starting material is a vegetable oil and fat, an animal oil and fat, a fish oil, an oil and fat produced by a microorganism, a mixture thereof or a waste oil thereof.

In one embodiment, the lower alcohol is methanol, ethanol, n-propanol, or n-butanol.

In a further embodiment, the method further comprising following the step (f): (f') repeating the steps (a) to (f) using the separated liquid obtained in the step (f) as the oil and fat starting material.

The present invention also provides an apparatus for continuously producing a fatty acid ester, comprising:

a plurality of stages of catalyst reaction tubes that are filled with a lipase;

a glycerin separation tank that is placed downstream of each of the catalyst reaction tubes, and that separates an outflowing liquid from the catalyst reaction tube into glycerin and a separated liquid;

a lower alcohol supply port that is placed upstream of each of the catalyst reaction tubes; and a mixing means that is placed between each of the lower alcohol supply ports and each of the catalyst reaction tubes for mixing an oil and fat starting material or the separated liquid and a lower alcohol;

wherein, in each stage of the catalyst reaction tubes, a mixture of the oil and fat starting material or the separated liquid from the glycerin separation tank and the lower alcohol is supplied from an upper portion of the catalyst reaction tube, and an out lowing liquid from a lower portion of the catalyst reaction tube is introduced into the glycerin separation tank.

In an embodiment, a liquid flow rate in the apparatus is adjusted to at least 2.15 cm/min.

In one embodiment, an amount of the lower alcohol supplied to each of the catalyst reaction tubes is adjusted to 0.5 to 1.0 mol equivalent with respect to the oil and fat starting material.

In a further embodiment, the number of stages of the catalyst reaction tubes is 2 to 10.

According to the present invention, in transesterification between an oil and fat and a lower alcohol using a lipase as a catalyst, it is possible to efficiently and continuously produce a fatty acid ester while automatically removing by-product glycerin. With the apparatus of the present invention, it is possible to efficiently and continuously perform a series of steps ranging from supply of starting materials to collection of a fatty acid ester.

BRIEF DESCRIPTION OF DRAWINGS

FIG. 6 is a graph showing the concentration of methyl ester in each stage in the case where a methanolysis reaction is repeatedly performed using two stages of catalyst reaction tubes.

BEST MODE FOR CARRYING OUT THE INVENTION

Lipase

Figure 1:
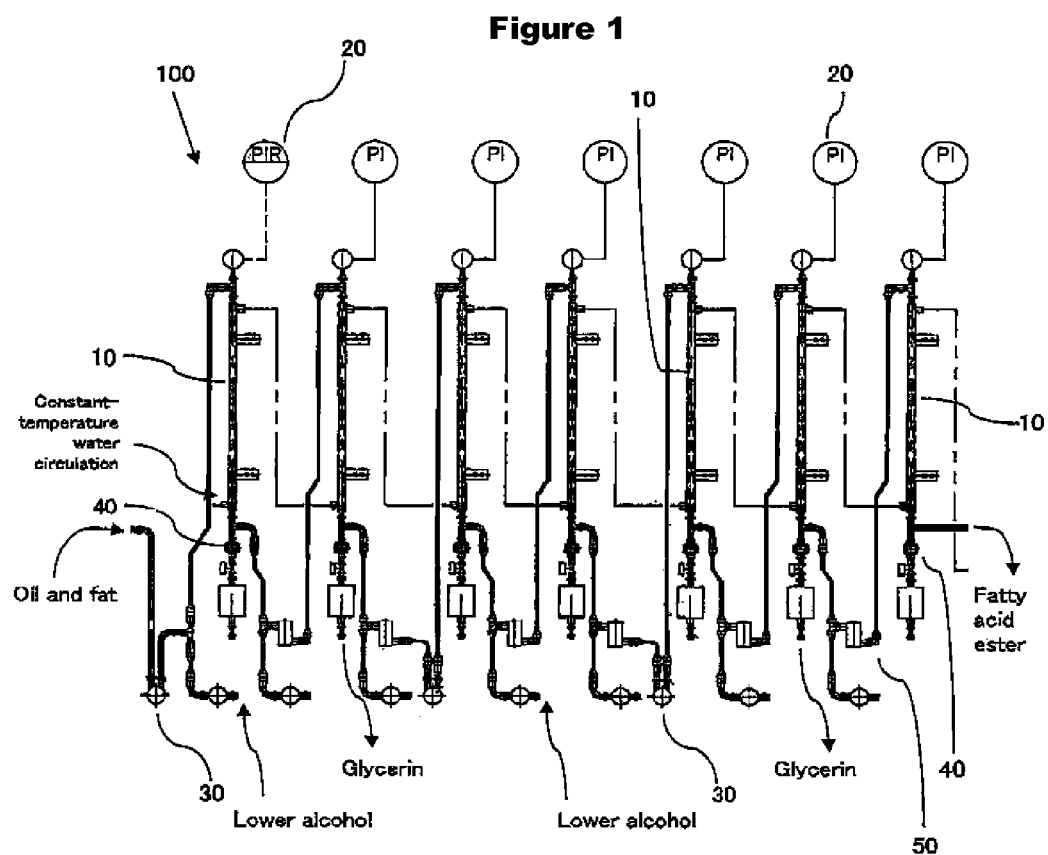
FIG. 1 is a schematic diagram showing the configuration of a reaction apparatus (packed-bed reactor) 100 of the present invention and the flow of continuous production of a biodiesel fuel using the same.

In the present invention, a lipase refers to an enzyme that has an ability to degrade glyceride (also referred to as acylglycerol) into glycerin or a partial glyceride and a fatty acid, and has an ability to produce a fatty acid ester through transesterification in the presence of a linear lower alcohol.

The lipase used in the present invention may be 1,3-specific or nonspecific. In view of production of a linear lower alcohol ester of a fatty acid, a nonspecific lipase is preferable. Examples of the lipase include: lipases derived from filamentous fungi belonging to Genus *Rhizomucor* (*Rhizomucor miehei*), *Mucor, Aspergillus, Rhizopus, Penicillium*, and the like; lipases derived from yeasts belonging to Genus *Candida* (*Candida antarctica, Candida rugosa*, and *Candida cylindracea*), *Pichia*, and the like; lipases derived from bacteria belonging to Genus *Pseudomonas, Serratia*, and the like; and lipases derived from animals, such as hog pancreas. Commercially available lipases are also used. Examples thereof include lipases derived from

*Rhizomucor miehei* (Lipozyme IM60: manufactured by Novo Nordisk), lipases derived from *Candida antarctica* (Novozyme 485: manufactured by Novozymes), lipases derived from *Rhizopus delemar* (Talipase: manufactured by Tanabe Seiyaku Co., Ltd.), lipases of *Candida rugosa* (Lipase OF: manufactured by Meito Sangyo Co., Ltd.), and lipases of the genus *Pseudomonas* (Lipase PS and Lipase AK: manufactured by Amano Enzyme Inc).

In the present invention, an immobilized lipase refers to a lipase that is immobilized on a given carrier. It is possible to use an immobilized enzyme that is immobilized on a commonly used carrier, such as a resin, or to use a cell that produces and retains the lipase. Furthermore, as described later, the cell may be further immobilized on a given carrier. Furthermore, it is effective to use mutually different types of immobilized lipases in each of the catalyst reaction tubes.

As the lipase that is immobilized on a carrier, ordinarily, a purified enzyme or a partially purified enzyme isolated or extracted from a natural product or a recombinant is used. Examples of the carrier on which a purified enzyme or a partially purified enzyme is immobilized include carriers usually used for immobilizing an enzyme. Examples thereof include organic high molecular compounds, such as various ion-exchange resins, and inorganic porous materials, such as ceramics. The immobilization is performed, for example, by applying methods usually used by those skilled in the art, such as a carrier-binding method, a crosslinking method, an entrapment method, and the like. The carrier binding method includes a chemical adsorption method or a physical adsorption method comprising adsorbing to an ion-exchange resin.

In the present invention, the cell that produces and retains the lipase is bacteria, fungi, plant cells, or the like, but there is no limitation thereto. It is preferable to use yeasts and filamentous fungi. It is also possible to use recombinants into which various lipase genes have been introduced.

The lipase-producing cell used in the present invention may be immobilized on a carrier. As the material of the carrier that can be used in the present invention, foams or resins such as polyvinyl alcohol, a polyurethane foam, a polystyrene foam, polyacrylamide, a polyvinyl formal resin porous material, a silicon foam, a cellulose porous material, or the like are preferable. It is preferable to use a porous carrier, for example, in view of shedding of cells with reduced growth and activity or dead cells. The size of the opening of the porous material varies depending on the type of cells. The size enough for cells to enter and grow therein is suitable. A size of 50 μm to 1000 μm is preferable, but the size is not limited thereto. There is no limitation regarding the shape of the carrier. In view of the strength of the carrier, the cultivation efficiency or the like, spherical or cubical shapes are preferable. A preferable size is 1 mm to 50 mm in diameter for a spherical carrier, and 2 mm to 50 mm in length of the side for a cubical carrier.

Starting Materials for Fatty Acid Ester

Starting materials for the fatty acid ester are an oil and fat and a lower alcohol.

As the oil and fat starting material, vegetable oils and fats, animal oils and fats, fish oils, oils and fats produced by microorganisms, mixtures thereof or waste oils thereof are used preferably. Examples of vegetable oils and fats include soybean oil, rape seed oil, palm oil, olive oil, and the like. Examples of animal oils and fat include beef tallow, lard, sperm oil, mutton tallow, and the like. Examples of fish oils include sardine oil, tuna oil, squid oil, and the like. Examples of oils and fats produced by microorganisms include oils and fats produced by microorganisms belonging to Genus *Mortierella*, *Schizochytrium*, and the like. The waste oils refer to used plant and animal oils and fats, and examples thereof include Tempura (battered and deep fried foods) waste oils, and the like. Since the waste oils were heated to a high temperature, they also contain hydrogenated, oxidized, or peroxidized oils. These oils also can be used as the starting material. The oils may contain water. Alternatively, the reaction mixture in which these oil and fat starting materials have once been treated with the lipase also can be used as the starting material.

A lower alcohol refers to an alcohol having 1 to 8 carbon atoms. A linear lower alcohol is preferable, in particular, methanol, ethanol, n-propanol, or n-butanol is preferable.

Reaction Apparatus

In the present invention, a reaction apparatus refers to an apparatus having a plurality of stages of connected catalyst reaction tubes that are tubes, such as stainless steel tubes, filled with an immobilized lipase or lipase-producing cells. FIG. 1 schematically shows the configuration of an embodiment of a reaction apparatus 100 as a typical apparatus of the present invention, using, as an example, the case in which the reaction apparatus is a packed-bed reactor, but there is no limitation thereto. This typical reaction apparatus 100 includes a plurality of stages of catalyst reaction tubes 10, glycerin separation tanks 40, lower alcohol supply ports, and a mixing means 60.

The catalyst reaction tubes 10 in FIG. 1 can be extended depending on the reaction efficiency. The catalyst reaction tubes 10 preferably have a length of 1 to 2 m per stage, and an inner diameter of 1 to 5 cm, but there is no limitation thereto. The number of stages of the catalyst reaction tubes 10 is preferably 2 to 10, and more preferably 8 to 7, but there is no limitation thereto. Furthermore, the catalyst reaction tubes 10 are preferably made of a material selected in consideration of the viscosity of the oil and fat, and deterioration caused by the starting materials and the product. Examples of such a material include stainless steel and the like.

The catalyst reaction tubes 10 are filled with the lipase that is immobilized by given means.

The catalyst reaction tubes 10 are connected to each other, for example, via tubes. The tubes connect the catalyst reaction tubes 10 such that an oil and fat starting material or a separated liquid is supplied to each catalyst reaction tube 10 from above, the separated liquid being obtained after passing through its preceding catalyst reaction tube 10 and the glycerin separation tank 40, and such that an outflowing liquid flows out of the lower portion of the catalyst reaction tube 10. Also, the tubes are preferably made of a material selected in consideration of the viscosity of the oil and fat, and deterioration caused by the starting materials and the product, and more preferably made of silicon or Teflon (registered trademark).

In this embodiment, pressure gauges 20 are arranged in order to measure the pressure in the catalyst reaction tubes 10. It is preferable to use pressure gauges that can indicate the pressure up to 1 MPa.

In this embodiment, pumps 30 are arranged in order to supply the starting materials (the oil and fat and the lower alcohol) and the separated liquid to the catalyst reaction tubes 10, or in order to supply the outflowing liquid to the glycerin separation tanks 40, at a given pressure or rate. It is preferable to use metering pumps having a maximum ejection pressure of approximately 0.4 to 1.0 MPa in consideration of a pressure loss in the catalyst reaction tubes 10.

Figure 2:
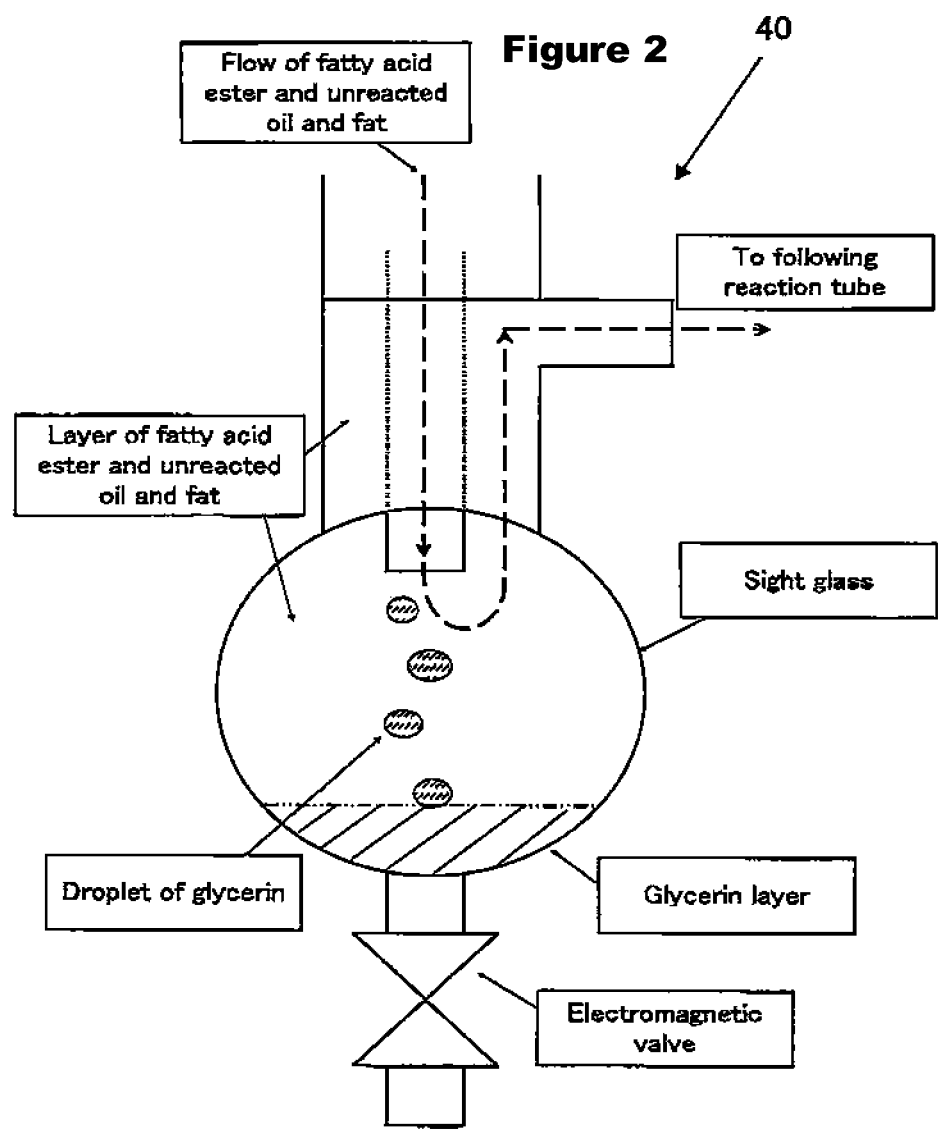
FIG. 2 is a schematic diagram showing a manner in which a fatty acid ester and glycerin are separated in a glycerin separation tank 40.

The glycerin separation tanks 40 are placed between the catalyst reaction tubes 10. There is no particular limitation regarding a method for separating glycerin. For example, as shown in FIG. 2, the glycerin separation tank 40 preferably has a space (e.g., a given space in a sight glass) for retaining the outflowing liquid from the catalyst reaction tube 10 (containing a fatty acid ester, unreacted oil and fat, and glycerin) for a given time. When the outflowing liquid is retained in the glycerin separation tank 40, a fatty acid ester and unreacted oil and fat, and glycerin that are contained in the outflowing liquid are separated into layers. The separated liquid containing the fatty acid eater and the unreacted oil and fat overflows and is supplied to the following catalyst reaction tube 10. The glycerin present in the lower layer is discharged downward when an electromagnetic valve is opened and closed after the elapse of a given time, and collected by a receiving unit. In this separation, as described later in detail, it is important to adjust the liquid flow rate (or the volume flow rate) in the reaction apparatus 100.

In the apparatus 100 of the present invention, lower alcohol supply ports are placed upstream of the respective stages of catalyst reaction tubes 10, and the lower alcohol is added from these supply ports to the separated liquid. Here, it is necessary to keep a uniformly dispersed state such that a droplet of the alcohol is not formed in the oil and fat, because the lower alcohol inhibits the activity of the lipase, and because the solubility of the lower alcohol to the oil and fat is extremely low. Therefore, in order to sufficiently mix the lower alcohol supplied immediately before each stage, and the oil and fat starting material or the outflowing liquid, the mixing means 50 is placed between the lower alcohol supply port and the following catalyst reaction tube. Examples of the mixing means 50 include fillers in the tube, and a stationary mixer. More specifically, for example, placing fillers such as beads in a tube for supplying the oil and fat or the separated liquid to the catalyst reaction tubes 10 can facilitate miring of a mixture of the oil and fat and the lower alcohol passing through the tube.

Furthermore, a constant-temperature water circulation apparatus is preferably placed around the catalyst reaction tubes 10. The constant-temperature water circulation apparatus preferably can keep the temperature of the reaction apparatus 100, in particular, the catalyst reaction tubes 10 at 25° C. to 45° C. at which the enzyme reaction occurs in a more preferable manner. Alternatively, the entire reaction apparatus 100, or the mixing means 50 and the catalyst reaction tubes 10 may be placed in a constant-temperature chamber.

Method for Producing Fatty Acid Ester

The present invention is directed to a method for continuously producing a fatty acid ester in a reaction apparatus having a plurality of stages of catalyst reaction tubes filled with a lipase, comprising:

(a) mixing and agitating an oil and fat starting material and a lower alcohol, and supplying a mixture to one of the catalyst reaction tubes;

(b) producing a fatty acid ester and glycerin in the catalyst reaction tube to which the oil and fat starting material and the lower alcohol are supplied;

(c) introducing an outflowing liquid from the catalyst reaction tube into a glycerin separation tank, thereby collecting the glycerin;

(d) adding a lower alcohol to a separated liquid obtained by separating the glycerin from the outflowing liquid, miring and agitating an obtained material, and supplying a mixture to a following catalyst reaction tube;

(e) repeating the steps (b) to (d) until supply to a last catalyst reaction tube is performed;

(f) introducing an outflowing liquid from the last catalyst reaction tube to a glycerin separation tank placed downstream of the last catalyst reaction tube, thereby collecting glycerin, and obtaining a separated liquid obtained by separating the glycerin from the outflowing liquid; and (g) collecting a fatty acid ester from the separated liquid obtained in the step (f).

In the present invention, it is possible to efficiently and continuously produce a fatty acid ester, for example, using the reaction apparatus 100 as shown in FIG. 1, as the reaction apparatus having a plurality of stages of catalyst reaction tubes filled with a lipase. That is to say in the reaction apparatus 100 described above, an oil and fat starting material and a lower alcohol are sufficiently agitated and supplied to the catalyst reaction tube 10, a lipase is caused to act in the catalyst reaction tube 10, thereby producing a fatty acid eater, the outflowing liquid from the catalyst reaction tube 10 is introduced into the glycerin separation tank 40, thereby glycerin being collected, and the separated liquid together with a lower alcohol is further supplied to the following catalyst reaction tube 10. By repeating these operations, a fatty acid ester can be collected from the separated liquid from the last catalyst reaction tube.

Alternatively, in the case where the number of stages of catalyst reaction tubes is small, the separated liquid from the last catalyst reaction tube may be used as the oil and fat starting material, and the reaction in this reaction apparatus may be repeated several times. For example, by repeatedly causing a liquid to pass three times through a reaction apparatus having three stages of catalyst reaction tubes, it is possible to obtain a separated liquid containing a fatty acid ester at the same concentration as that in a reaction apparatus having nine stages of catalyst reaction tubes.

In the reaction apparatus 100, it is important to adjust the liquid flow rate (or the volume flow rate) in the reaction apparatus 100. If the liquid flow rate is low, the separation efficiency of glycerin from the outflowing liquid in the glycerin separation tanks 40 is poor. The liquid flow rate is determined as appropriate depending to the type of alcohol, the diameter and the number of stages of the catalyst reaction tubes 10, the type of the oil and fat starting material, and the like. In the present invention, the liquid flow rate is usually at least 2.16 cm/min, preferably at least 4.65 cm/min, more preferably at least 6.08 cm/min, still more preferably at least 6.90 cm/min, even more preferably at least 7.76 cm/min, and most preferably at least 8.62 cm/min.

The amount and the rate of lower alcohol supplied are determined depending to the type of alcohol, the number of stages of the catalyst reaction tubes 10, the type of the oil and fat starting material, the flow rate, and the like. The amount of lower alcohol supplied to each stage is preferably kept at 0.5 to 1.0 mol equivalent with respect to the oil and fat starting material. If the amount of lower alcohol supplied is small, the productivity of methyl ester and the separation efficiency of glycerin are poor. On the other hand, if the amount of lower alcohol supplied is large, the activity of the lipase in the catalyst reaction tubes 10 may be inhibited. Furthermore, regarding the rate of lower alcohol supplied, for example, in the case where a triolein starting material is caused to pass through the catalyst reaction tubes 10 at 1000 ml/h, the rate of methanol supplied is preferably 19.9 to 89.9 ml/h. Causing the lower alcohol to pass through the mixing means 50, such as fillers in the tube, a stationary mixer, or the like can facilitate miring of the lower alcohol and the oil and fat.

Transesterification between the oil and fat and the lower alcohol catalysed by the lipase is performed generally at 5° C. to 80° C., preferably at 15° C. to 50° C., and more preferably at 25° C. to 45° C. The reaction temperature may be determined depending on a microorganism or an enzyme used. For example, in the case where a heat-resistant microorganism or enzyme is used, the reaction can be performed at a relatively high temperature.

The fatty acid ester after the reaction is separated and collected from the reaction mixture containing unreacted glyceride and lower alcohol through a separating operation usually used by those skilled in the art, such as distillation. The thus collected fatty acid ester can be used as a biodiesel fuel.

EXAMPLE

Example 1

Reaction Apparatus

FIG. 1 shows a schematic diagram showing the configuration of the packed-bed reactor 100 used in Examples. Stainless steel pipes (length 1 m, inner diameter 15.7 mm, and volume 193.6 ml) were used as the catalyst reaction tubes 10. These stainless steel pipes were filled with Novozyme 485 (manufactured by Novozymes) to an enzyme filling ratio of 60% (v/v) to give the catalyst reaction tubes 10. The catalyst reaction tubes 10 were kept at 30° C., and the pressure gauges 20 were placed above the tubes to confirm a pressure loss. The oil and fat starting material was supplied to the upper portion of the catalyst reaction tube 10 using the metering pump 80, and fillers were placed inside a supply tube for the catalyst reaction tube 10, thus facilitating mixing of the oil and fat and the lower alcohol.

Furthermore, the glycerin separation tanks 40 were placed under the catalyst reaction tubes 10, and glycerin formed as a by-product during the reaction procedure was collected in each stage. As shown in FIG. 2, in the glycerin separation tank 40, the fatty acid ester, the unreacted oil and fat, and the glycerin contained in the outflowing liquid from the catalyst reaction tube 10 were retained in a given space in a sight glass, and the separated liquid (containing the fatty acid eater and the unreacted oil and fat) obtained by the separation performed therein and a newly added lower alcohol were supplied to the following catalyst reaction tube 10 while being sufficiently mixed by the mixing means 50.

Example 2

Transesterification

First, 500 g of refined vegetable oil (Shirashime oil) was used as the oil and fat starting material, 9.07 g of methanol (0.5 mol equivalents with respect to the oil and fat) was added to each stage, end the mixture was caused to pass through the catalyst reaction tube 10. Here, the volume flow rate at the catalyst reaction tubes 10 was set to 250 ml/h, 640 ml/h, or 1080 ml/h. These volume flow rates at the catalyst reaction tubes 10 respectively correspond to liquid flow rates of 2.15 cm/min, 4.65 cm/min, and 9.30 cm/min. After the oil and fat starting material was caused to pass, the valves in the lower portions of the glycerin separation tanks 40 were opened, and the weight of by-product glycerin formed in each stage was measured. Then, 200 µl of the separated liquid flowing out in each stage was collected, and the concentration (content) of fatty acid methyl ester was analyzed.

The concentration (content) of fatty acid methyl ester (wt %) was determined by a gas chromatography analysis using tricaprylin as the internal standard. The analysis conditions were as follows.

Column: ZB-5HT (manufactured by Phenomenex, inner diameter 0.25 mm, length 15 m)
Column temperature:
Initial: 130° C., 2 min
Temperature rise: 350° C., 10° C./min
380° C., 7° C./min
Final temperature: 380° C., 10 min
Injector temperature: 320° C.
Detector temperature: 380° C.
Carrier gas: helium gas (1.76 ml/min)
Split ratio: 1/50

Figure 3:
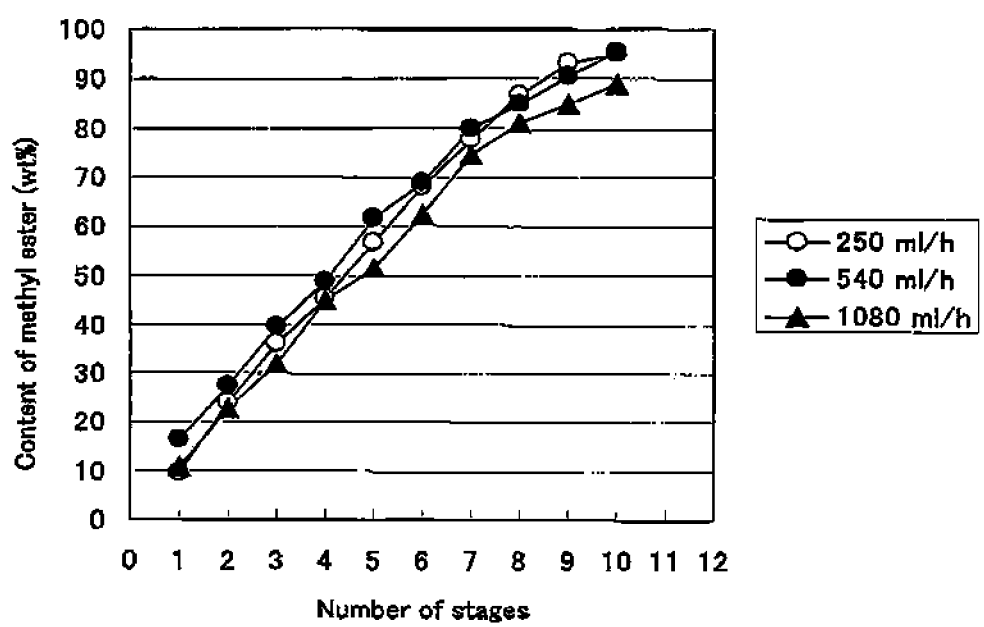
FIG. 3 is a graph showing the concentration of fatty acid ester in a liquid flowing out of each stage of a catalyst reaction tube 10 at a volume flow rate of 250 to 1080 ml/h (a liquid flow rate of 2.15 to 9.80 cm/min).

FIG. 3 shows the content of fatty acid methyl ester in the separated liquid obtained in each stage. As the number of stages increased, the content of methyl ester in the outflowing liquid increased, and the concentrations in the ninth stage were respectively 98.8 wt % (volume flow rate 250 m/h), 90.6 wt % (540 ml/h), and 84.8 wt % (1080 ml/h), and those in the 10th stage were respectively 96.8 wt % (540 m/h) and 88.9 wt % (1080 m/h). The concentration of methyl ester in the separated liquid obtained in each stage was affected by a change in the volume flow rate, in other words, the retention time in the catalyst reaction tubes 10, but it was shown that a sufficiently high concentration of methyl ester was obtained even with a relatively short retention time (approximately 10.8 min per stage at 1080 ml/h).

Figure 4:
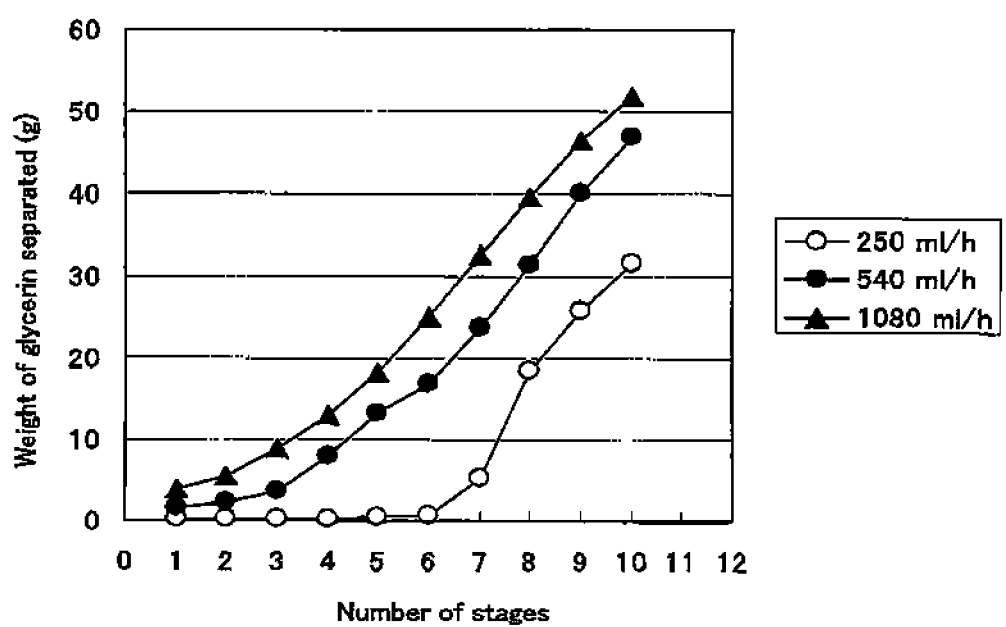
FIG. 4 is a graph showing the weight of glycerin separated in the glycerin separation tank 40 placed downstream of each stage of the catalyst reaction tube 10.

FIG. 4 shows the weight (cumulative amount) of glycerin collected by the separation tank 40 in each stage. In the case where 500 g of oil and fat is completely converted to a fatty acid methyl ester, the total amount of glycerin formed as a by-product is approximately 52.04 g. In the case where the volume flow rate was 250 ml/h, glycerin was not practically collected even in the sixth stage where the content of methyl ester was greater than 68 wt %. This means that since the flow rate of the outflowing liquid was low, a glycerin layer was retained near the enzyme in the catalyst reaction tubes 10. In the case where the volume flow rate was 540 ml/h, the weight of glycerin separated increased as the number of stages increased, and 46.8 g of glycerin was separated in stages up to the 10th catalyst reaction tube 10 where the content of methyl ester reached 95.8 wt %. This figure corresponds to 89.9% of the amount of glycerin that can be theoretically separated. Furthermore, in the case where the volume flow rate was 1080 ml/h, 51.75 g of glycerin (99.4% of the theoretical amount) was separated in stages up to the 10th catalyst reaction tube 10.

Example 3

Investigation on Reaction Conditions

Table 1 lists the number of stages in the packed-bed reactor used in this Example, the concentration of fatty acid ester after the reaction in 10 stages, the productivity per unit reaction time and per unit reactor volume, the weight of glycerin separated, and the ratio of the glycerin amount with respect to the theoretical amount.

TABLE 1

| Volume flow rate (ml/h) | Liquid flow rate (cm/min) | Number of stages | Content of methyl ester (wt %) | Productivity (g/h/L) | Weight of glycerin separated (g) | Ratio of glycerin amount with respect to theoretical amount (%) |
|---|---|---|---|---|---|---|
| 250 | 2.15 | 10 | 95.0 | 106.7 | 31.5 | 60.5 |
| 540 | 4.65 | 10 | 95.3 | 231.3 | 46.8 | 89.9 |
| 1080 | 9.30 | 10 | 88.9 | 431.4 | 51.8 | 99.4 |

It was shown that, with the same conditions as in Example 2, in the case where the oil and fat starting material or the separated liquid was caused to pass through the catalyst reaction tubes at a volume flow rate of 540 ml/h or more, that is, at a liquid flow rate of 4.65 em/min or more, glycerin corresponding to approximately 90% of the theoretical amount was separated, and that, in the case where the volume flow rate was 1080 ml/h (the liquid flow rate was 9.80 cm/min), glycerin corresponding to 99% or more of the theoretical amount was separated. In the case where 10 stages of catalyst reaction tubes were taken as one reactor, the productivity of methyl ester per unit reaction time and per unit reactor volume was 106.7 g/h/L (250 ml/h), 281.3 g/h/L (540 ml/h), and 431.4 g/h/L (1080 ml/b). As described by Y. Shimada et al. (Journal of Molecular Catalysis B: Enzymatic, 2002, Vol. 17, pp. 133-142), in the case where an oil and fat in an equal volume to that of the reactor is treated under batch-type reaction conditions using the same enzyme, and a product having a final concentration of methyl ester of 97.3 wt % is obtained after a reaction time of 48 hours, the productivity is estimated as 17.6 g/h/L. Therefore, it is shown that the process for producing the fatty acid ester in the present invention is extremely advantageous in view of separation of the product and the by-product, and the productivity of the fatty acid ester per unit reaction time and per unit reactor volume.

Figure 5:
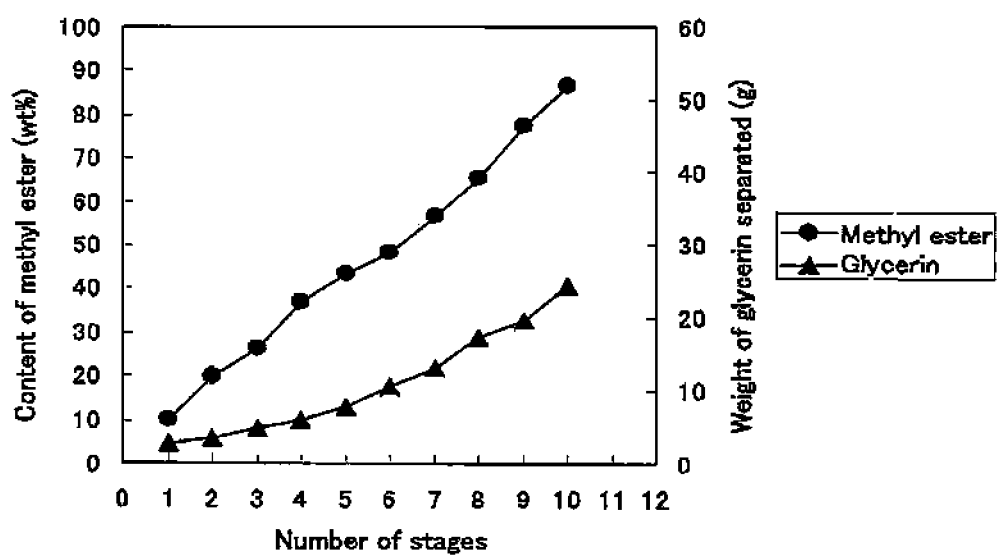

Next, 0.88 mol equivalents of methanol with respect to the oil and fat were mixed therewith in each stage, and the mixtures was caused to pass through the stage at a volume flow rate of 540 ml/h. FIG. 5 shows the content of methyl ester and the outflow amount of glycerin (cumulative amount) in this case. Under these conditions, the productivity of methyl ester and the separation efficiency of glycerin in each stage were inferior to those in the case where 0.5 mol equivalents of methanol with respect to the oil and fat starting material were mixed therewith. Accordingly, it is shown that adjustment of the amount of methanol supplied to the catalyst reaction tubes significantly affects the apparatus ability.

Example 4

Figure 6:
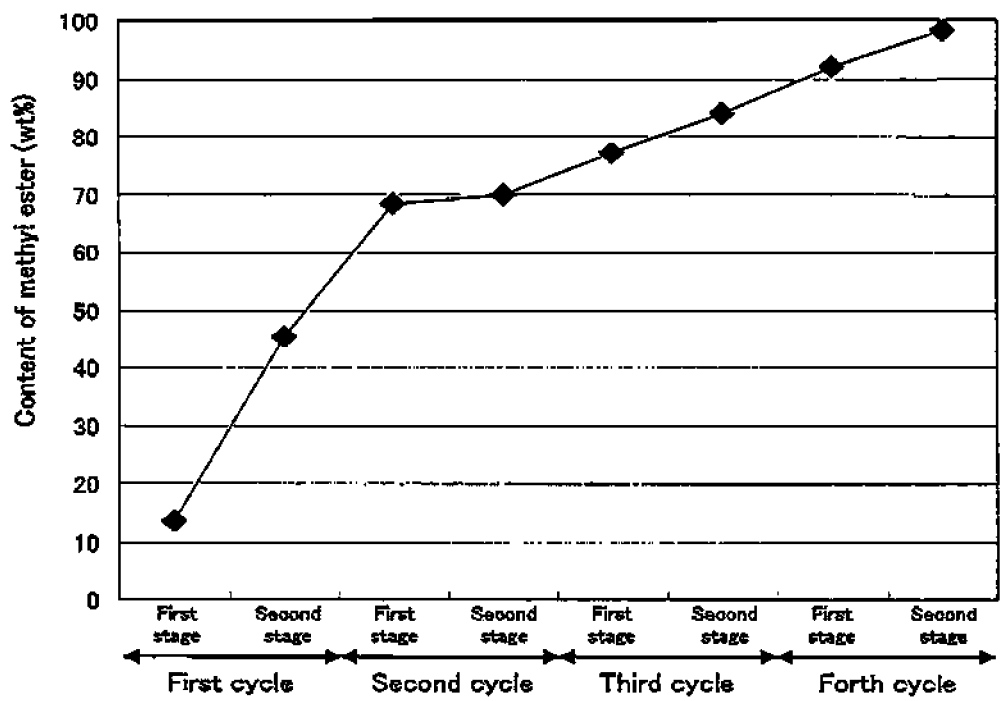
FIG. 6 is a graph showing the concentration of methyl ester and the outflow amount of glycerin in the case where 0.88 mol equivalents of methanol with respect to an oil and fat starting material are mixed with a liquid that is to be supplied to each stage of the catalyst reaction tube 10, and the mixture liquid is caused to pass through the tube at a volume flow rate of 540 ml/h (a liquid flow rate of 4.65 cm/min).

Investigation on Continuous Production Using Two Stages of Catalyst Reaction Tubes In this Example, the number of stages of the catalyst reaction tubes 10 was set to two in the packed-bed reactor 100 shown in FIG. 1. First, 0.5 mol equivalents of methanol with respect to the oil and fat were mixed therewith before each of a first and a second catalyst reaction tube 10, and the oil and fat was caused to pass through the tubes at a volume flow rate of 540 ml/h (first cycle). Glycerin was separated from the oil and fat flowing out of the second catalyst reaction tube 10, 0.5 mol equivalents of methanol with respect to the oil and fat were mixed therewith, and then the oil and fat was again caused to pass through the first catalyst reaction tube 10 as in the first cycle (second cycle). The same operation was repeated two more times. FIG. 6 shows the content of fatty acid methyl ester in the separated liquid obtained in each stage.

FIG. 6 clearly shows that, in the case where a methanolysis reaction was repeated four times in the two stages of catalyst reaction tubes, a fatty acid ester having a high purity was obtained. It is shown that, in the case where a liquid is continuously and repeatedly caused to pass through a reactor having two stages of catalyst reaction tubes in this manner, a fatty acid ester having a high purity can be obtained as in the case where a reactor having many stages of catalyst reaction tubes is used. Therefore, it is shown that the cost of the apparatus can be reduced by reducing the number of stages of catalyst reaction tubes.

INDUSTRIAL APPLICABILITY

According to the method of the present invention, a fatty acid ester can be produced through a continuous procedure of adding a lower alcohol without stopping the reaction, and automatically separating by-product glycerin, and thus, production efficiency is high, and production cost can be reduced. Furthermore, the separated glycerin does not require special washing treatment, and thus, the environmental load is low, and the produced fatty acid ester is provided as a biodiesel fuel with less environmental pollution.

The invention claimed is:
1. A method for continuously producing a fatty acid ester in a reaction apparatus having a plurality of stages of catalyst reaction tubes filled with a lipase, comprising:
(a) mixing and agitating an oil and fat starting material and a lower alcohol, and supplying a mixture to one of the catalyst reaction tubes;
(b) producing a fatty acid ester and glycerin in the catalyst reaction tube to which the oil and fat starting material and the lower alcohol are supplied;
(c) continuously introducing an outflowing liquid from the catalyst reaction tube into a separation tank having an opening at the top that is placed under the catalyst reaction tube,
wherein the outflowing liquid flows out from the lower portion of the catalyst reaction tube which is lower than the opening at the top of the separation tank, and is introduced into the separation tank,
wherein the outflowing liquid introduced into the separation tank is separated into lower and upper layers of the glycerin and a separated liquid, thereby the glycerin is collected from the lower layer, and the separated liquid of the upper layer overflows from the opening at the top of the separation tank, and
wherein the separated liquid contains fatty acid ester and unreacted oil and fat;

(d) adding a lower alcohol to the separated liquid, mixing and agitating an obtained material, and supplying a mixture to a following catalyst reaction tube;
(e) repeating the steps (b) to (d) until supply to a last catalyst reaction tube is performed;
(f) obtaining a separated liquid obtained by separating the glycerin from the outflowing liquid; and
(g) collecting a fatty acid ester from the separated liquid obtained in the step (f).

2. A method according to claim 1, wherein a liquid flow rate in the reaction apparatus is at least 2.15 cm/min.

3. A method according to claim 1, wherein an amount of the lower alcohol supplied to each of the catalyst reaction tubes is 0.5 to 1.0 mol equivalent with respect to the oil and fat starting material.

4. A method according to claim 1, wherein the number of stages of the catalyst reaction tubes is 2 to 10.

5. A method according to claim 1, wherein the oil and fat starting material is a vegetable oil and fat, an animal oil and fat, a fish oil, an oil and fat produced by a microorganism, a mixture thereof, or a waste oil thereof.

6. A method according to claim 1, wherein the lower alcohol is methanol, ethanol, n-propanol, or n-butanol.

7. A method according to of claim 1, further comprising following the step (f): (f) repeating the steps (a) to (f) using the separated liquid obtained in the step (f) as the oil and fat starting material.

* * * * *

UNITED STATES PATENT AND TRADEMARK OFFICE
CERTIFICATE OF CORRECTION

PATENT NO. : 9,879,291 B2
APPLICATION NO. : 14/741755
DATED : January 30, 2018
INVENTOR(S) : Nobuyuki Kuratani et al.

It is certified that error appears in the above-identified patent and that said Letters Patent is hereby corrected as shown below:

In the Specification

At Column 3, Line 28, "2.16" should read --2.15--.

At Column 4, Line 28, "9.80" should read --9.30--;
    Line 32, "6" should read --5--; and
    Line 34, "0.88" should read --0.33--.

At Column 5, Line 3, "48.5:" should read --435--.

At Column 6, Line 31, "8" should read --3--.

At Column 8, Line 41, "2.16" should read --2.15--;
    Line 42, "6.08" should read --6.03--; and
    Line 59, "89.9" should read --39.9--.

At Column 9, Line 25, "485" should read --435--;
    Line 31, "80" should read --30--; and
    Line 59, "640" should read --540--.

At Column 10, Line 26, "98.8" should read --93.3--;
    Line 28, "96.8" should read --95.3--; and
    Line 51, "95.8" should read --95.3--.

At Column 11, Line 20, "9.80" should read --9.30--;
    Line 24, "281.3" should read --231.3--;
    Line 25, "(1080ml/b)." should read --(1080ml/h).--; and
    Line 38, "0.88" should read --0.33--.

Signed and Sealed this
Tenth Day of April, 2018

Andrei Iancu
*Director of the United States Patent and Trademark Office*

In the Claims

At Column 13, Line 25, "(f)" should read --(f')--.